United States Patent [19]

Saperstein et al.

[11] Patent Number: 5,919,158
[45] Date of Patent: Jul. 6, 1999

[54] METHOD AND APPARATUS FOR PREVENTING AND CLEARING CONDENSATION ON THE LENS DURING A FLUID-GAS EXCHANGE PORTION OF A PARS PLANA VITRECTOMY

[75] Inventors: David A. Saperstein; Michael D. Bennett, both of Atlanta, Ga.

[73] Assignee: Emory University, Atlanta, Ga.

[21] Appl. No.: 08/799,132

[22] Filed: Feb. 13, 1997

[51] Int. Cl.[6] .................................................... A61M 31/00
[52] U.S. Cl. ................................. 604/49; 623/6; 604/280
[58] Field of Search ............................. 604/49, 289, 294, 604/23, 24, 19, 280, 264; 623/4, 5, 6

[56] References Cited

U.S. PATENT DOCUMENTS

| 4,795,423 | 1/1989 | Osterholm . |
| 5,336,175 | 8/1994 | Mames . |
| 5,360,399 | 11/1994 | Stegmann . |

OTHER PUBLICATIONS

Weinberg, R.S., et al., Histopathology after Vitrectomy with the Vitrophage, Ophthalmologies, Albert von Graefe's Archive for Clinical and Experimental Ophthalmology, vol. 196, No. 2, pp. 133–42, Aug. 6, 1975.

Ozdemir, O., et al., Results of Pars Plana Vitrectomy in Behcet's Disease, Annals of Ophthalmology, vol. 20, No. 1, pp. 35, 38, Jan. 1988.

Sappenfield, D., et al, Impaired Ophthalmoscopy and Condensation on Intraocular Lens, American Journal of Ophthalmology, vol. 108., No. 1, p. 88, Jul. 15, 1989.

Slusher, M..M., et al., Loss of Visibility Caused By Moisture Condensation on the Posterior Surface of a Silicon Intraocular Lens During Fluid/Gas Exchange After Posterior Vitrectomy, American Journal of Ophthalmology, vol. 118, No. 5, p. 667, Nov. 15, 1994.

Eaton, A.M., et al., Condensation on the Posterior Surface of Silicone Intraocular Lenses During Fluid–Air Exchange, Journal of the American Academy of Ophthalmology, vol. 102, No. 5, pp. 733–36, May 1995.

Bartz–Schmidt, K.U., et al., Condensation On IOLS During Fluid–Air Exchange, Journal of the American Academy of Ophthalmology, vol. 103, No. 2, p. 199, Feb. 1996.

Kusaka, S., et al., Condensation of Silicone Oil on the Posterior Surface of a Silicone Intraocular Lens During Vitrectomy, American Journal of Ophthalmology, vol. 121, No. 5, pp. 574–75, May, 1996.

*Primary Examiner*—John D. Yasko
*Attorney, Agent, or Firm*—John S. Pratt; Bruce D. Gray; Kilpatrick Stockton LLP

[57] ABSTRACT

An infusion cannula for use in clearing and preventing condensation on the posterior surface of an artificial lens during the fluid-gas exchange portion of a pars plana vitrectomy is described. The infusion cannula directs the flow of gas entering the eye toward the posterior surface of the lens. The moisture content of the gas supplied to the infusion cannula is minimized in order to increase the effectiveness with which condensation is removed or prevented. Additionally, the temperature of the gas supplied to the infusion cannula is controlled to further increase the effectiveness with which condensation is removed.

23 Claims, 5 Drawing Sheets

METHOD AND APPARATUS FOR PREVENTING AND CLEARING CONDENSATION ON THE LENS DURING A FLUID-GAS EXCHANGE PORTION OF A PARS PLANA VITRECTOMY

This invention relates to a method and apparatus for preventing and clearing condensation from the surface of an artificial intraocular lens in the eye during the fluid-gas exchange portion of a pars plana vitrectomy. More particularly the invention relates to an apparatus for redirecting the flow of air, which may also be dried or cooled or both, toward the surface of the intraocular lens during the fluid-gas exchange portion of a pars plana vitrectomy.

BACKGROUND OF THE INVENTION

During vitreoretinal surgery, the surgeon views the interior of the eye through the patient's cornea and lens. Because the interior of the eye is the portion on which the surgical procedure is being performed, it is critical that a vitreoretinal surgeon be able to see into the eye at all times during surgery.

In order to repair a rhegmatogenous detachment of the retina (in which the neurosensory retina is torn or cut, allowing fluid to collect underneath it), the surgeon first removes the vitreous humor (or any other liquid or gas in the eye) and fills the eye with balanced saline solution, for example. The surgeon then performs a fluid-gas exchange procedure in which the saline solution is removed at the same volumetric rate as a gas (usually sterile air from the operating room) is injected. As the gas replaces the fluid, any subretinal fluid is squeezed from under the retina and readily removed with an extrusion cannula. Once all the saline solution is removed, the surgeon seals the retinal hole, tear, or cut with endolaser photocoagulation, for example, and either leaves the air in the eye or replaces the gas with a tamponade of silicone oil or a long-lasting inert gas like $C_3F_8$ or $SF_6$.

The surgeon's vision is often impaired during the fluid-gas exchange by water or silicone droplets that condense on the posterior surface of the lens in (or just posterior to) the anterior chamber of the eye. This condensation can make it difficult or impossible to see and repair the retinal detachment. Other cases have been reported in which the condensation persists post-operatively and impairs the patient's vision.

The formation of condensation during the fluid-gas exchange portion of the vitrectomy is particularly common and troublesome on the posterior surface of silicone lenses in eyes on which a capsulotomy has been performed. The results of one study published in the May 1995 issue of *Ophthalmology* at pages 733–36 indicated that condensation occurred in 11 of 11 patients who had a silicone lens and a capsulotomy. The same study indicated that no condensation occurred in 7 of 7 patients who had silicone lenses without a capsulotomy.

Various methods of removing water condensation from silicone lenses have been tried, with limited success. In the May 1995 study discussed above, attempts to remove the condensation with a soft-tipped aspiration cannula partially cleared the condensation in 6 of the 11 patients in which condensation occurred, but the condensation quickly reappeared to completely obscure the surgeon's vision after only one to two minutes. The May 1995 study also suggested that water condensation might be more effectively removed by applying a thin film of silicone oil to the lens. However, the film has been found to coalesce into silicone droplets on the lens surface. These silicone droplets significantly impaired the surgeon's vision into the eye and were even more difficult to remove than water condensation. Others have reported that a fluid-gas exchange performed on a patient's eye previously filled with silicone oil and having a silicone lens resulted in inoperative silicone condensation that could not be removed. Therefore, this method has been found appropriate only in those patients in which the eye will be filled with silicone oil as a long-term tamponade. The authors of the May 1995 study have recommended, however, that the silicone oil tamponade be used only as a last resort, when other approaches have failed.

Doctors Sappenfield, Cohen, and Gitter described another approach to clearing water condensation from the lens in the July 1989 issue of the *American Journal of Ophthalmology*. Sappenfield et al. suggested inserting an angled cannula through the sclerotomy and injecting a balanced salt solution onto the posterior surface of the lens. This approach was reported to have successfully removed the water condensation in one particular case, but it requires injection of fluid into an eye from which the surgeon is trying to remove fluid. Adding fluid in this manner delays and thus impairs the fluid-gas exchange.

Sappenfield et al. also suggested warming lens using the intraocular irrigating solution (which fills the eye before the fluid-gas exchange portion of the vitrectomy) or introducing a small amount of viscoelastic material (e.g., hyaluronic acid) onto the posterior surface of the lens. It has also been suggested that filling the anterior chamber of the eye with warm viscoelastic fluid would warm the lens sufficiently to prevent condensation. While these approaches may succeed in temporarily clearing water condensation, they require constant manipulation of the instruments that deliver irrigation solution and leave a film of fluid on the posterior lens that distorts the surgeon's view into the eye. Thus, retinal surgeons commonly believe that using warm irrigation solutions or depositing viscoelastic fluids on the posterior lens is at best a temporary and unsatisfactory method of clearing water condensation that requires added and unwanted manipulation of instruments during surgery.

Condensation has also been observed during the fluid-gas exchange procedure on the posterior surface of other types of artificial lenses including polymethylmethacralate (PMMA), acrylic, hydragel, and heparin-coated PMMA lenses. While water condensation on these lenses has not been reported to be as widespread or persistent a problem, the proposed solutions for preventing and clearing water condensation from silicone lenses are not completely effective on these other lenses. Thus, a need continues to exist for a quick, simple, and long-lasting method for removing water condensation during the fluid-gas exchange portion of a pars plana vitrectomy from the posterior surface of an artificial lens.

SUMMARY OF THE INVENTION

The present invention improves upon prior art methods and devices by obviating the need for any added procedure for preventing and clearing condensation during the fluid-gas exchange and avoiding complications caused by introducing silicone oil, saline solution, hyaluronic acid, or other fluids during the fluid-gas exchange. The present invention employs three important changes to prior instruments used to perform the fluid-gas exchange. First, the infusion cannula used to infuse gas into the eye is formed such that it directs the flow of gas toward the posterior surface of the lens. Second, the moisture content of the gas is minimized. Third, the temperature of the gas is controlled.

The most effective method of preventing or clearing condensation on the posterior surface of the lens uses all three approaches described above. That is, a dried and cooled stream of air is directed so that it continuously flows over the posterior surface of the lens. However, it has been found that continuously directing the flow of typical room air (without any drying or cooling) toward the posterior surface of the lens during surgery often sufficiently prevents or clears water condensation. Such a continuous directed flow of infusion air may be accomplished by the surgeon positioning a conventional straight infusion cannula so that its outlet points at the posterior surface of the lens. However, this method requires an added degree of skill and constant attention by the surgeon because it requires that the surgeon physically hold the infusion cannula in a particular orientation rather than simply suturing the cannula in place and letting the sutures hold it in position.

In order to accomplish more easily the required flow of air over the posterior surface of the lens, the surgeon may use a specially-formed infusion cannula according to the present invention having an outlet that directs the gas toward the posterior surface when the cannula is otherwise conventionally sewn into a sclerotomy in the eye. Such an infusion cannula, once appropriately inserted into the sclerotomy, requires no more attention from the surgeon than does a conventional straight cannula. Thus, the use of such a cannula prevents or clears condensation on the posterior surface of the lens without requiring any further manipulation by the surgeon during surgery.

For example, such a specially formed infusion cannula may have an outlet in its distal end (as does a conventional straight infusion cannula) and be bent at a location distal from the sclerotomy so that the outlet faces the posterior surface of the lens when sewn into position within the sclerotomy. Alternatively, the infusion cannula may be straight but have an outlet or outlets in its side wall so that air exiting the infusion cannula is directed toward the posterior surface of the lens. In both types of infusion cannulae, the handle may be marked to indicate quickly and conveniently to the surgeon the direction in which air exits the cannula. This marking would allow the surgeon to orient efficiently the infusion cannula to ensure that the air flow is correctly directed toward the posterior surface of the lens. Of course, other geometries for the infusion cannula exist that may accomplish the desired redirection of air flow toward the posterior surface of the lens, and these geometries are all within the scope and spirit of the present invention.

The effectiveness of the infusion cannulae according to the present invention is increased by reducing the moisture content of the infusion gas and by controlling the temperature of the infusion gas. The moisture and the temperature may be controlled by conventional methods adapted for use with sources of ophthalmic infusion gas. For example, dry air, which is commonly available in commercial quantities, may be supplied in a pressurized tank and used as a source of infusion gas, with appropriate pressure controls of course. Alternatively, a conventional pump may be used to gather and supply high pressure room air, which is then dehumidified before being supplied to a conventional pressure controller.

It is accordingly an object of the present invention to prevent or clear condensation on the posterior surface of an artificial lens by using an infusion cannula that effectively directs air flow toward the posterior surface of the lens while positioned otherwise conventionally within a sclerotomy during eye surgery.

It is a further object of the present invention to provide an apparatus for controlling the moisture content of the gas supplied to the interior of the eye via an infusion cannula during the fluid-gas exchange portion of a vitrectomy.

It is a further object of the present invention to provide an apparatus for controlling the temperature of the gas supplied to the interior of the eye via an infusion cannula during the fluid-gas exchange portion of a vitrectomy.

Other objects, features and advantages of the present invention will become apparent with reference to the remainder of this document.

DETAILED DESCRIPTION OF THE DRAWINGS

Figure 1:
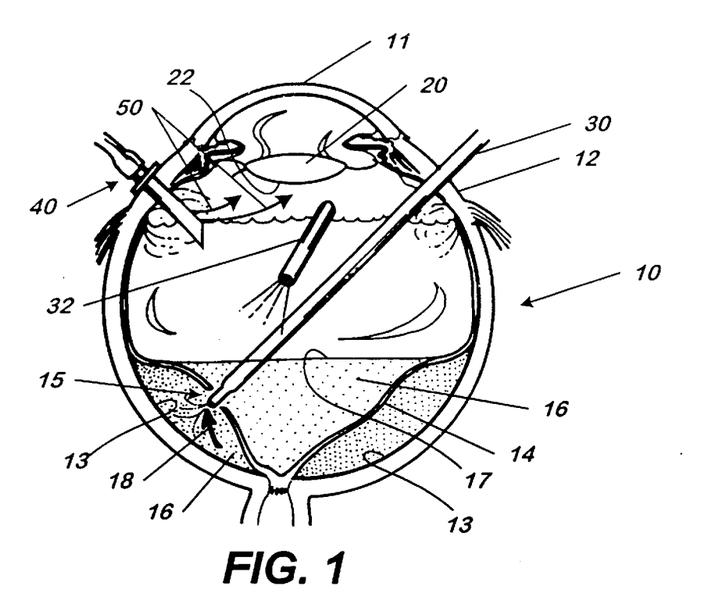
FIG. 1 is a schematic cross-sectional representation of a patient's eye as gas is infused into the eye to replace fluid using an infusion cannula according to the present invention.
Figure 2:
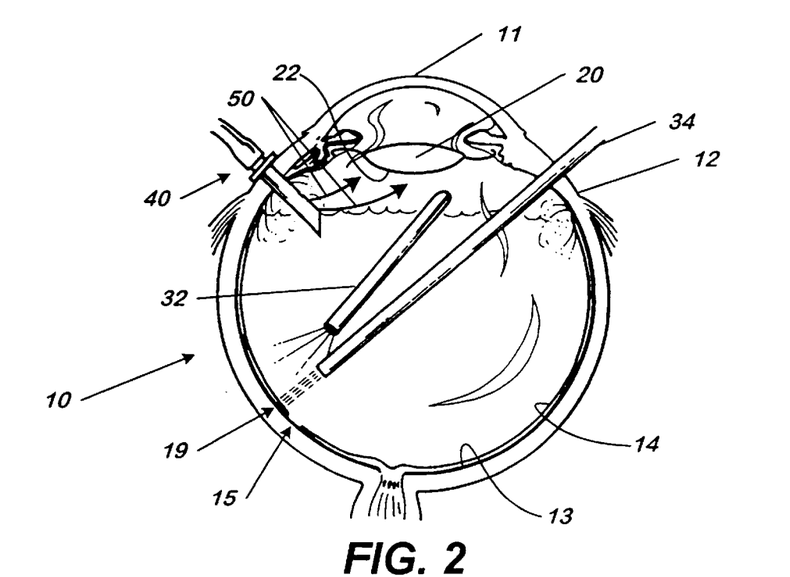
FIG. 2 is a schematic cross-sectional representation of a patient's eye after the fluid has been replaced with gas and depicting photocoagulation of the retinotomy.

FIGS. 1 and 2 illustrate the use of an infusion cannula 40 according to the present invention during the fluid-gas exchange portion of a pars plana vitrectomy on a patient having an artificial lens 20 implanted in the anterior chamber. In general, FIG. 1 illustrates the fluid-gas exchange and FIG. 2 illustrates photocoagulation of the retinotomy 15 using a laser 34. During the vitrectomy, the surgeon views the interior of the eye 10 through the cornea 11 and the artificial lens 20. As described above, the surgeon's view into the eye is often blocked by condensation forming on the posterior surface 22 of lens 20. When such condensation is present, the surgeon often is unable to continue with the procedure.

In order to clear such condensation and thus render possible the fluid-gas exchange, subsequent endolaser, and other intraocular manipulations, the surgeon performs the fluid-gas exchange using infusion cannula 40 according to the present invention. Because the cannula is sewn in at the outset of the surgery, the surgeon need not perform any additional maneuvers to prevent or clear the condensation other than allowing for an egress of gas from the eye and thus flow of gas across the posterior side of the lens. For example, the surgeon may clear the condensation, as perhaps shown best in FIG. 1, by inserting infusion cannula 40 (shown in detail in FIGS. 3–6) through a first sclerotomy and extrusion cannula 34 through a second sclerotomy. Light probe 32 is inserted through a third sclerotomy in order to illuminate the area on which the surgeon is working. Gas, preferably dry air, enters the interior of eye 10 through ports in infusion cannula 40 such that the gas generally flows in the directions indicated by arrows 50 toward the posterior surface 22 of lens 20. In order to enable the surgeon to direct effectively the flow of gas toward the posterior surface 22 of lens 20, infusion cannula 40 includes an indicator (shown in FIG. 6 by reference numeral 45) which corresponds the direction in which the gas is flowing from infusion cannula 40.

As gas fills eye 10, it exerts pressure upon fluid surface 17, which forces fluid 16 out through extrusion cannula 30. This may be enhanced by active suction through extrusion cannula 30. As gas replaces fluid 16, it squeezes all fluid 16 from between eye wall 13 and retina 14 through retinotomy 15 as indicated by arrow 18. The gas also forces the remaining fluid 16 out of the interior of eye 10 and forces retina 14 to "lay down" on the eye wall 13 (i.e., the retinal pigment epithelium). Once, retina 14 is returned to this position on the eye wall 13, which is perhaps best shown in FIG. 2, the surgeon tacks the retina 14 to the eye wall 13 using a laser probe 34 inserted through the second sclerotomy to cause photocoagulation of retina 14 to eye wall 13.

FIGS. 3–6 provide a detailed graphic illustration of infusion cannula 40, which is a preferred embodiment of an infusion cannula according to the present invention. As is perhaps best illustrated in FIGS. 3 and 4, infusion cannula 40 includes a relatively long tubular body 42 defining side walls of infusion cannula 40 and having a portion 42a inserted into flexible tubing 48, which communicates with the supply of gas. Gas enters the proximal end of tubular body 42 and exits infusion cannula 40 through ports 46 as depicted by arrow 50 of FIG. 4. The face 41 forms a beveled distal end of tubular body 42 at angle α, which eases insertion of infusion cannula 40 into a patient's eye through a sclerotomy. The proximal end of tubular body 42, of course, is open and thus pneumatically communicates with the supply of the gas through tubing 48. Annular projection 44 protrudes radially from tubular body 42 at a location proximally spaced from the distal end of tubular body 42. Distal surface 44a of projection 44 provides a stop that prevents infusion cannula 40 from further penetrating the sclerotomy. Proximal surface 44b of projection 44 provides support for indicator 45 (shown in FIG. 6) and allows the surgeon to more easily suture infusion cannula 40 into place in the sclerotomy so that the infusion cannula 40 need not be held in place by hand during surgery.

Figure 3:
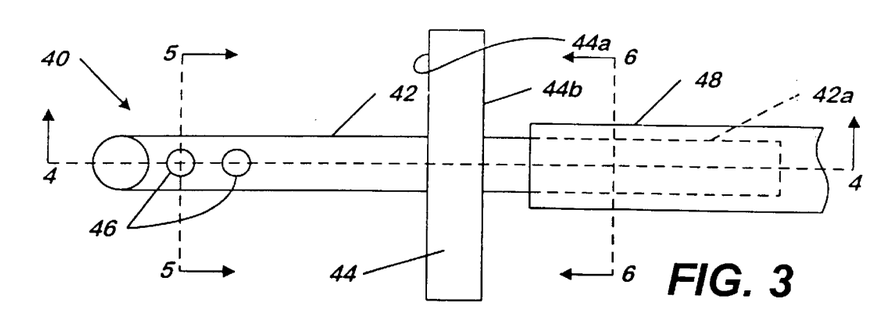
FIG. 3 is a plan view of a preferred embodiment of an infusion cannula according to the present invention.
Figure 4:
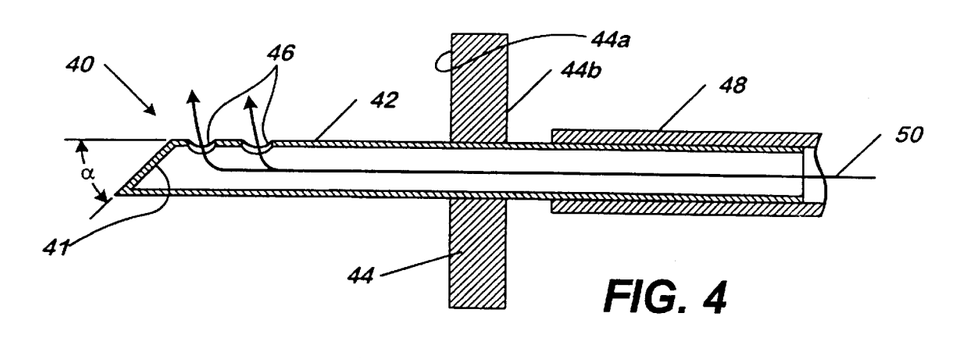
FIG. 4 is a cross-sectional view of the infusion cannula of FIG. 3 taken along line 4—4.
Figure 5:
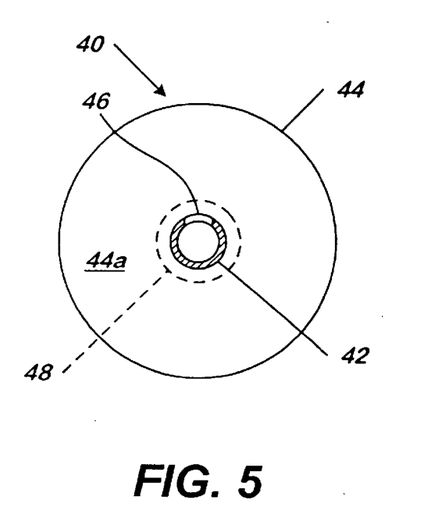
FIG. 5 is a cross-sectional view of the infusion cannula of FIG. 3 taken along line 5—5.
Figure 6:
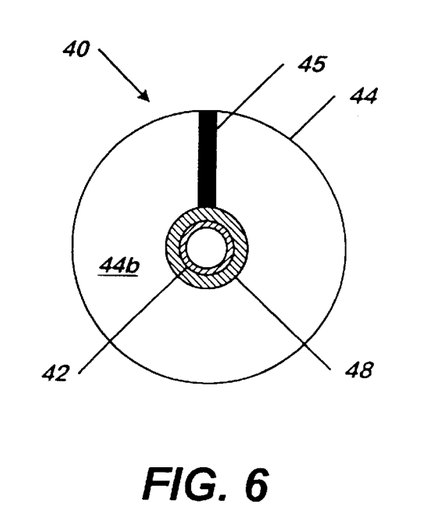
FIG. 6 is a cross-sectional view of the infusion cannula of FIG. 3 taken along line 6—6.

FIGS. 5 and 6 are cross sectional views from a distal and proximal perspective respectively that further illustrate tubular body 42, annular projection 44, and tubing 48. As illustrated by the combination of FIGS. 3, 5, and 6, indicator 45 is substantially aligned with ports 46 so that the surgeon can determine the orientation of ports 46, and therefore the direction in which gas will flow from infusion cannula 40, when infusion cannula 40 is positioned within the sclerotomy during surgery.

Figure 7:
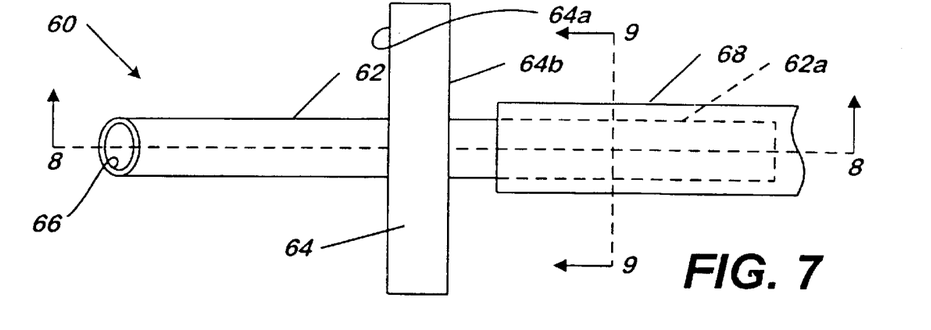
FIG. 7 is a plan view of a second embodiment of an infusion cannula according to the present invention.
Figure 8:
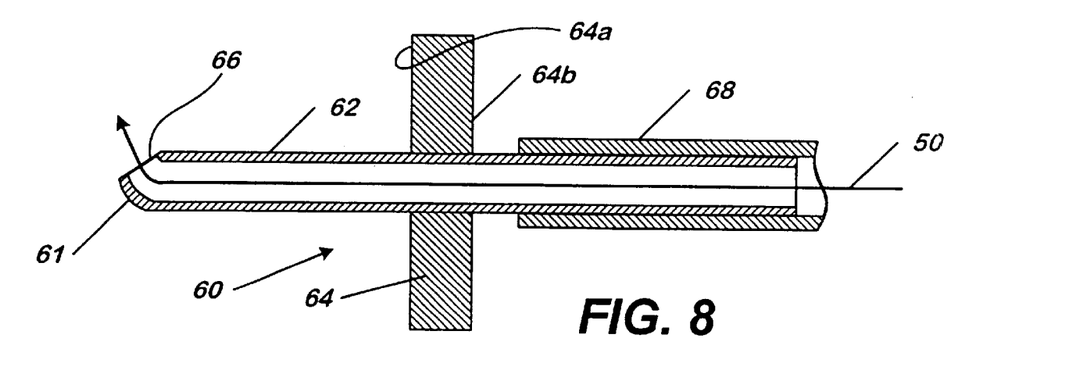
FIG. 8 is a cross-sectional view of the infusion cannula of FIG. 7 taken along line 8—8.
Figure 9:
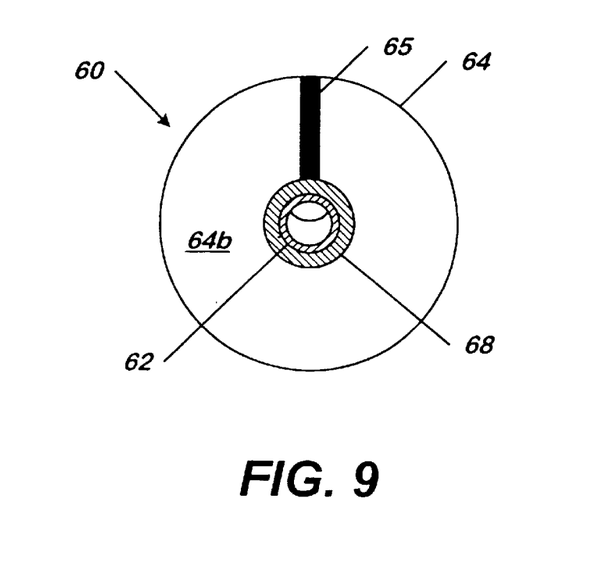
FIG. 9 is a cross-sectional view of the infusion cannula of FIG. 7 taken along line 9—9.

FIGS. 7–9 illustrate a second embodiment of an infusion cannula according to the present invention. As is seen in FIGS. 7 and 8, infusion cannula 60 is similar to infusion cannula 40 except that it includes only one port 66, which is located in the distal end of tubular body 62. Gas is directed upward by a bend 61 in the distal end of tubular body 62 rather than by radially located ports 46 in tubular body 42 of infusion cannula 40. Just as described in connection with infusion cannula 40, a proximal portion 62a of infusion cannula 60 is inserted into tubing 68, which communicates pneumatically with a supply of gas. Annular projection 64, surfaces 64a and 64b, and indicator 65 (shown in FIGS. 7 and 9) perform the same functions as those performed by projection 44, surfaces 44a and 44b, and indicator 45 respectively as described in FIGS. 3–6.

Figure 10:
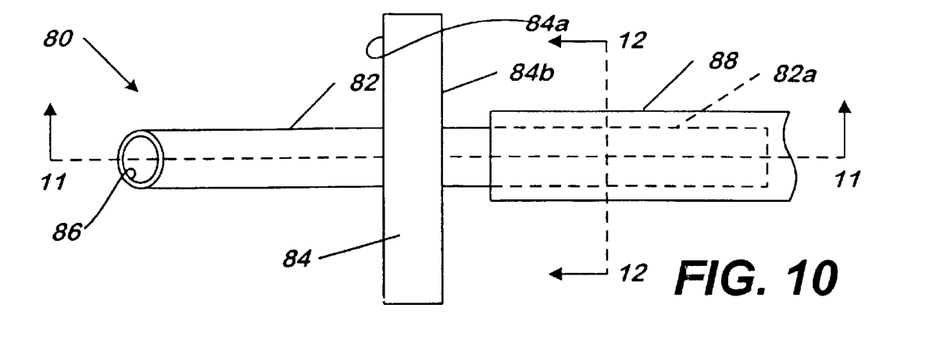
FIG. 10 is a plan view of a third embodiment of an infusion cannula according to the present invention.
Figure 11:
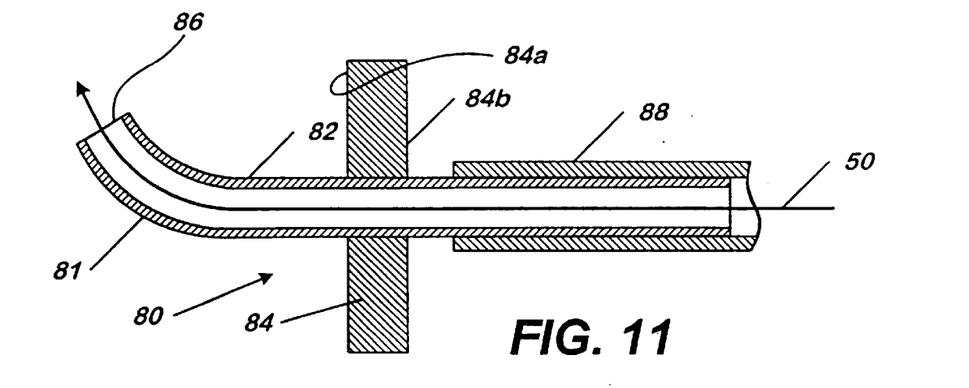
FIG. 11 is a cross-sectional view of the infusion cannula of FIG. 10 taken along line 11—11.
Figure 12:
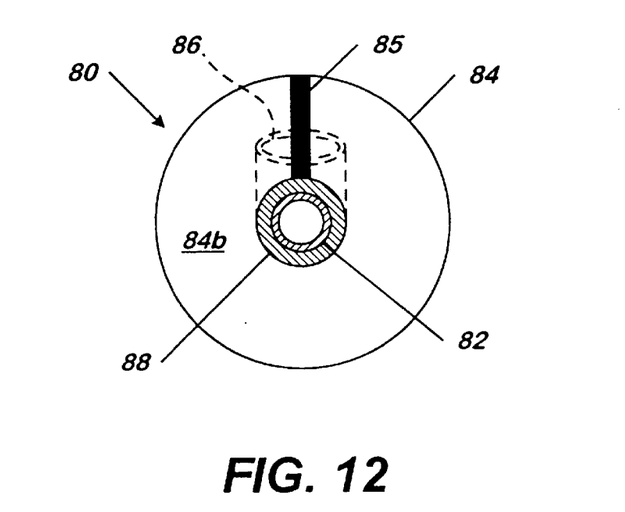
FIG. 12 is a cross-sectional view of the infusion cannula of FIG. 10 taken along line 12—12.

FIGS. 10–12 illustrate a third embodiment of an infusion cannula according to the present invention. As is seen in FIGS. 10 and 11, infusion cannula 80 is similar to infusion cannula 60 except that bend 81 occurs over a greater length of tubular body 82 than bend 61 in infusion cannula 60. Bend 81 directs gas upward similarly to bend 61. Although not shown in FIGS. 10–12, bend 81 could also be a sharp angle having a distinct joint and have similar effect on the flow of gas as does bend 81 as shown. Just as described in connection with infusion cannula 60, a proximal portion 82a of infusion cannula 80 is inserted into tubing 88, which communicates pneumatically with a supply of gas. Annular projection 84, surfaces 84a and 84b, and indicator 85 (shown in FIGS. 10 and 12) perform the same functions as those performed by projection 64, surfaces 64a and 64b, and indicator 65 respectively as described in FIGS. 7–9.

Of course, the particular position, size, and shape of the various elements of infusion cannulae 40, 60, and 80 shown in FIGS. 3–12 are illustrative of an infusion cannula according to the present invention, but not exhaustive all possible types of cannulae. Essentially, any infusion cannula that functions to direct gas flow toward the posterior surface of the lens in the eye in order to clear or prevent condensation on that surface is within the scope of the invention.

Figure 13:
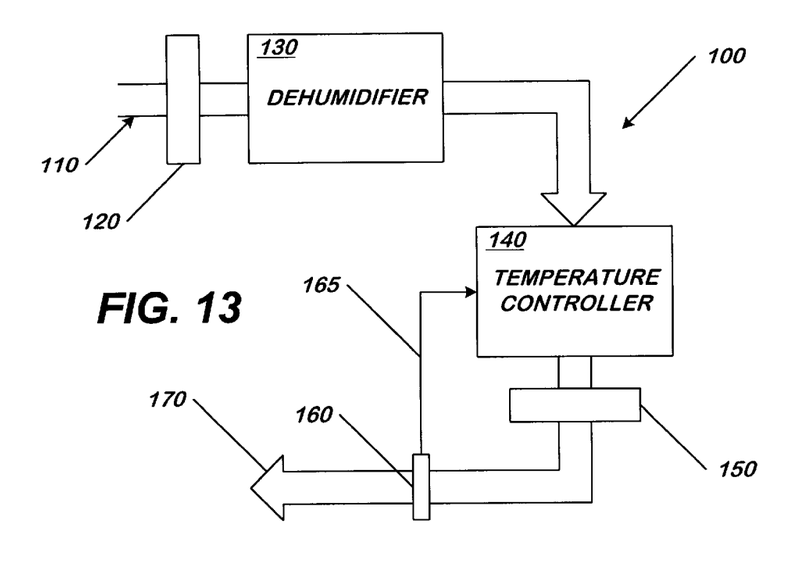
FIG. 13 is a schematic illustration of an ophthalmic surgical system including an infusion cannula according to the present invention.

FIG. 13 is a schematic illustration of a temperature and moisture control portion of an ophthalmic surgical system suitable for use with an infusion cannula according to the present invention. Air may be drawn into intake 110 of temperature and moisture controller 100 and routed through sterilizing filter 120 to dehumidifier 130. Dehumidifier 130 may employ any number of conventional methods of removing moisture from air including a conventional air conditioning thermodynamic cycle. Little or no closed loop control is required for dehumidifier 130 because the infusion gas should be as dry as possible for maximum effectiveness at preventing and clearing condensation. After the gas is dehumidified, it is routed to temperature controller 140, which may be any type of heat exchanger that does not introduce moisture into the gas. Temperature controller 140 may either heat or cool the gas, but cooled gas has been found experimentally to clear more effectively condensation than heated gas. The gas is then passed through another sterilizing filter 150 and the temperature of the gas is measured by sensor 160, which is preferably located as close to the infusion cannula (which is connected to exhaust 170) as possible. Temperature sensor 160 generates a feedback signal 165 suitable for use by the control logic of temperature controller 140 that enables the temperature of the gas to be more closely regulated. All components shown in FIG. 13 are conventional and known.

Figure 14:
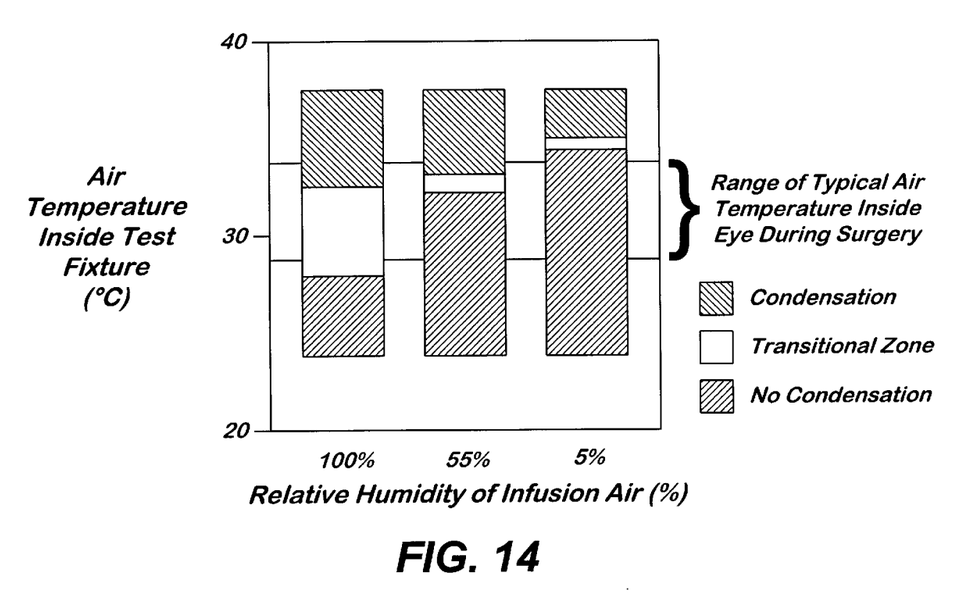
FIG. 14 is a graphic representation of results of experiments during which the air temperature at which condensation occurred on the lens was recorded for three different levels of relative humidity of infusion air.

FIG. 14 is a graphic representation of the results of experiments in which the temperatures at which condensation on the lens started to occur and became heavy were recorded for three different levels of relative humidity of the infusion air source. The results for each level of relative humidity is shown as one bar graph. The air temperature inside the test fixture is shown along the vertical axis, and the relative humidity of the air as it was infused into the test fixture (not the relative humidity of the air once inside the test fixture) is shown under each bar graph. The test fixture was an enclosed clear cylinder having an infusion opening and an extrusion opening. A pressurized source of infusion air (at a pressure of about 35 mm Hg) was connected to the infusion opening, and a length of open exhaust tubing was connected to the extrusion opening. A silicone lens was mounted in the top end of the cylinder and was visible during the entirety of each experiment. The flow of infusion air was not directed toward the lower surface of the lens during the experiments, but rather into the center of the test fixture. The air temperature inside the test fixture was continuously measured and recorded as it increased from a starting temperature of about 24° C. to a temperature of about 37° C. Some liquid water was always present in the bottom of the test fixture during each of the experiments.

The first experiment was conducted using air that was saturated (100% relative humidity) at 24° C. and the results are depicted in the bar on the left of FIG. 14. As the air temperature inside the test fixture increased to about 28° C., light condensation began to form on the lens. Droplets formed on the lens at about 32° C. and grew heavier as the temperature increased further. Thus, for the experiment using infusion air of 100% relative humidity, no condensation occurred at temperatures below about 28° C., irregular and light condensation occurred between about 28° C. and 32° C. (the transitional zone), and heavy condensation occurred at temperatures above about 32° C.

The second experiment was conducted using air of about 55% relative humidity at 24° C. and the results are depicted in the bar in the center of FIG. 14. As the air temperature inside the test fixture increased to about 31.5° C., light condensation began to form on the lens. Droplets formed on the lens at about 33° C. and grew heavier as the temperature increased further. Thus, for the experiment using infusion air of 55% relative humidity at 24° C., no condensation occurred at temperatures below about 31.5° C., irregular and light condensation occurred between about 31.5° C. and 33° C. (the transitional zone), and heavy condensation occurred at temperatures above about 33° C.

The third experiment was conducted using virtually dry air of about 5% relative humidity at 24° C. and the results are depicted in the bar on the right of FIG. 14. As the air temperature inside the test fixture increased to about 35° C., light condensation began to form on the lens. Droplets formed on the lens at about 36° C. and grew heavier as the temperature increased further. Thus, for the experiment using infusion air of 5% relative humidity at 24° C., no condensation occurred at temperatures below about 35° C., irregular and light condensation occurred between about 35° C. and 36° C. (the transitional zone), and heavy condensation occurred at temperatures above about 36° C.

As shown by the gray band that spans all three bar graphs of FIG. 14, the typical range of observed air temperatures inside a human eye during surgery is about 29° C. to 34° C. Thus, when very dry air (of about 5% relative humidity at 24° C.) is used as an infusion gas, condensation likely will not occur on the lens. The warmer the air inside the eye, the more likely that moisture inside the eye will evaporate and increase the relative humidity of the air. The higher the moisture content of the air (i.e., the higher the dew point), the more likely that condensation will occur on the lens. Thus, a cooler atmosphere inside the eye appears to be more effective at preventing and clearing condensation on the lens. However, warm dry air that is circulated quickly through the eye (so that the dew point of the air does not increase from evaporation of moisture inside the eye) could also effectively prevent or clear condensation on the lens.

The use of any of the cannulae according to the present invention enables the use of almost any type of infusion air (as long as it is not saturated) to prevent or clear condensation. It is believed that this is true because directing the flow of infusion air to the posterior lens effectively controls the local dew point immediately adjacent the surface of the lens. That is, the moisture inside the eye does not evaporate quickly enough to humidify the incoming air stream as it enters the eye and strikes the lens. Because the infusion air is always being replenished, evaporation into the infusion air after it has circulated past the surface of the lens does not cause condensation on the lens. The use of drier infusion air would, however, render a cannula according to the present invention even more effective at preventing and clearing condensation.

While certain embodiments of the present invention have been described above, these descriptions are given for purposes of illustration and explanation. Variations, changes, modifications and departures from the devices and methods disclosed above may be adopted without departure from the scope or spirit of the present invention which, in sum, functions to lower the dew point of the atmosphere immediately adjacent the posterior surface of the lens during a fluid-gas exchange in order to prevent or clear condensation on the lens.

We claim:

1. An infusion cannula for use in performing surgery on an eye in which an artificial intraocular lens has been implanted, comprising:
   a. a hollow tube having a proximal end defining a longitudinal axis and adapted to be pneumatically connected to an infusion source, a distal end, and a first direction substantially corresponding to the longitudinal axis and
   b. an opening near the distal end adapted to direct a gas supplied from the infusion source in a second direction different from the first direction.

2. The infusion cannula of claim 1, in which the opening is located in a side wall of the tube.

3. The infusion cannula of claim 2, further comprising an indicator disposed near the proximal end of the tube allowing a surgeon to discern the orientation of the second direction in which the gas exits the opening.

4. The infusion cannula of claim 1, in which the tube is curved at a point between the proximal end and the distal end and the opening is in the distal end of the tube.

5. The infusion cannula of claim 4, further comprising an indicator disposed near the proximal end of the tube allowing a surgeon to discern the orientation of the second direction in which the gas exits the opening.

6. An ophthalmic surgical system for use in performing a vitrectomy on an eye in which an artificial intraocular lens has been implanted, comprising:
   a. an infusion source of a gas to be supplied to the interior of the eye and
   b. an infusion cannula having a proximal end pneumatically connected to the infusion source, a distal end adapted for insertion into the eye, a longitudinal axis at the proximal end that defines a first direction, and an opening near the distal end adapted to direct the gas in a second direction different from the first direction.

7. The ophthalmic surgical system of claim 6, further comprising a conditioner pneumatically disposed between the infusion source and the infusion cannula and adapted to remove moisture from the gas and to maintain the gas delivered to the infusion cannula at a predetermined temperature.

8. The ophthalmic surgical system of claim 6, in which the opening in the infusion cannula is located in a side wall of the infusion cannula.

9. The ophthalmic surgical system of claim 8, further comprising an indicator disposed near the first end of the infusion cannula allowing a surgeon to discern the orientation of the second direction in which the gas exits the opening.

10. The ophthalmic surgical system of claim 6, in which the infusion cannula is curved at a point between the proximal end and the distal end and the opening is in the distal end of the infusion cannula.

11. The ophthalmic surgical system of claim 10, in which the infusion cannula further comprises an indicator disposed near the proximal end of the infusion cannula allowing a surgeon to discern the orientation of the second direction in which the gas exits the opening.

12. A gas conditioner for use in an ophthalmic surgical system, comprising:
   a. an inlet adapted to communicate pneumatically with an infusion source of a gas to be supplied to the interior of a patient's eye;
   b. an outlet adapted to communicate pneumatically with an infusion cannula to be inserted into an eye; and
   c. means for adjusting the moisture content of the gas that is pneumatically disposed between the inlet and the outlet.

13. The gas conditioner of claim 12, further comprising means for maintaining the temperature of the gas exiting the outlet at a predetermined temperature value that is pneumatically disposed between the inlet and the outlet.

14. A gas conditioner for use in an ophthalmic surgical system, comprising:
   a. an inlet adapted to communicate pneumatically with an infusion source of a gas to be supplied to the interior of a patient's eye;
   b. an outlet adapted to communicate pneumatically with an infusion cannula to be inserted into an eye; and
   c. a moisture controller pneumatically disposed between the inlet and the outlet that maintains the moisture content of the gas exiting the outlet at a predetermined moisture value.

15. The gas conditioner of claim 14, further comprising a temperature controller pneumatically disposed between the inlet and the outlet that maintains the temperature of the gas exiting the outlet at a predetermined temperature value.

16. The gas conditioner of claim 15, in which the temperature controller and the moisture controller comprise a compressor-based refrigeration device.

17. A method of preventing condensation on the posterior surface of a lens in a patient's eye during the fluid-gas exchange portion of a vitrectomy, comprising the steps of:
   a. inserting an infusion cannula into the eye;
   b. inserting an extrusion instrument into the eye;
   c. infusing a first fluid into the eye through the infusion cannula while simultaneously removing a preexisting fluid from the eye through the extrusion instrument;
   d. infusing a gas supplied through the infusion cannula into the eye by positioning the infusion cannula to direct the gas toward the posterior surface of the lens within the eye while simultaneously removing the first fluid from the eye through the extrusion instrument.

18. The method of claim 17, in which the infusion cannula is bent at a location along its length between a distal end and a proximal end of the infusion cannula that is positioned inside the eye during the step in which gas is infused into the eye.

19. The method of claim 17, in which the infusion cannula comprises an opening in a side wall of the infusion cannula near an end of the infusion cannula that is inserted into the eye.

20. The method of claim 17, further comprising the step of conditioning the gas before performing the step of infusing the gas into the eye.

21. The method of claim 20, in which the step of conditioning the gas further comprises maintaining the moisture content of the gas at a predetermined moisture level.

22. The method of claim 20, in which the step of conditioning the gas further comprises maintaining the temperature of the gas at a predetermined temperature level.

23. The method of claim 22, in which the step of conditioning the gas further comprises maintaining the moisture content of the gas at a predetermined moisture level.

* * * * *